United States Patent
Otera et al.

(10) Patent No.: US 6,201,131 B1
(45) Date of Patent: Mar. 13, 2001

(54) PROCESS FOR PRODUCING [2-(ARYLSULFONYL) ETHENYL] BENZENE DERIVATIVES

(75) Inventors: Jyunzou Otera; Akihiro Orita, both of Okayama; Akio Kurihara, Toyonaka, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/533,110

(22) Filed: Mar. 22, 2000

(30) Foreign Application Priority Data

Mar. 24, 1999 (JP) .................................................. 11-079479

(51) Int. Cl.$^7$ ..................... C07D 209/04; C07D 311/04; C07D 307/78; C07C 309/00
(52) U.S. Cl. ............................ 548/469; 562/87; 549/290; 549/398; 549/469
(58) Field of Search .............................. 548/469; 562/87; 549/290, 398, 469

(56) References Cited

U.S. PATENT DOCUMENTS

| | | |
|---|---|---|
| 5,545,644 | 8/1996 | Macor et al. . |
| 5,902,905 | 5/1999 | Seko et al. . |

FOREIGN PATENT DOCUMENTS

| | | |
|---|---|---|
| 4-17182 | 3/1992 | (JP) . |
| WO9206973 | 4/1992 | (WO) . |

OTHER PUBLICATIONS

DeVito, Stephen C., "Designing Safer Chemicals: Toxicological Considerations", *CHEMTEC*, pp. 34–37 (Nov. 1996).

Lee et al., A Practical and Large Scale Synthesis of Phenyl Vinyl Sulfone from Benzenethiol and 2–Chloroethanol, Bulletin of the Korean Chemical Society, 16(7) :670–672 (1995).

*Primary Examiner*—Joseph K. McKane
*Assistant Examiner*—Joseph Murray

(74) *Attorney, Agent, or Firm*—Birch, Stewart, Kolasch & Birch, LLP

(57) ABSTRACT

The present invention provides a safer and more efficient process for producing [2-(arylsulfonyl)ethenyl]benzene derivatives of the formula (3):

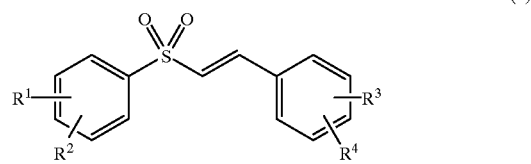

(3)

wherein $R^1$, $R^2$, $R^3$ and $R^4$ are the same or different and each independently represent a hydrogen, fluorine, or chlorine atom, a lower alkyl group, or the like, and two adjacent $R^3$ and $R^4$ may bond each other at their terminals to form a ring, which the process is characterized in that a 2-(arylsulfonyl)ethanol of formula (1):

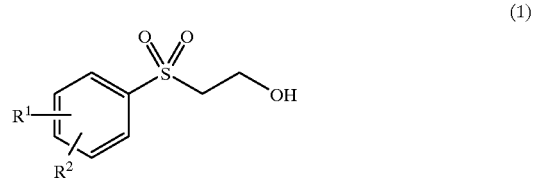

(1)

wherein $R^1$ and $R^2$ are as defined above, and an acid anhydride are reacted in the presence of a base, and the reaction liquid obtained is supplied to a reaction with an aromatic halide of formula (2):

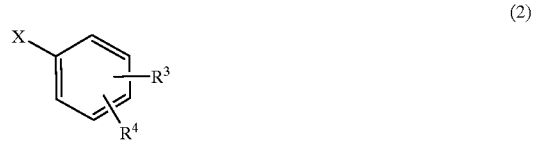

(2)

wherein X represents a chlorine, bromine, or iodine atom, and $R^3$ and $R^4$ are the same as defined above, in the presence of a palladium catalyst and a base.

7 Claims, No Drawings

PROCESS FOR PRODUCING [2-(ARYLSULFONYL) ETHENYL] BENZENE DERIVATIVES

BACKGROUND OF THE INVENTION

1. Field of the Invention

The present invention relates to a process for producing [2-(arylsulfonyl)ethenyl]benzene derivatives, which are useful as intermediates to pharmaceuticals, agricultural chemicals or the like.

2. Description of Related Art

It has been known that certain [2-(Arylsulfonyl)ethenyl] benzene derivatives have been produced from aryl vinyl sulfones (e.g., Japanese Patent Publication Kohyo No. H5-507288 (1993)). The aryl vinyl sulfones such as phenyl vinyl sulfones have been known as an irritant and have been isolated as a solid compound from a reaction mixture and charged into a reactor in a solid form. Such handling is inevitably accompanied by scattering of aryl vinyl sulfone dusts, laborious solid material handling and hence exposure of workers to the undesirable working environment in terms of safety and health (The Sigma-Aldrich Library of Chemical Safety Data, 2808 (1988) and Chemtech, Novvember, 34 (1996)).

SUMMARY OF THE INVENTION

An object of the invention is to provide a safer and more efficient process for producing [2-(arylsulfonyl)ethenyl] benzene derivatives, which process does not require the handling of solid aryl vinyl sulfones.

The present invention provides:

a process for producing [2-(arylsulfonyl)ethenyl]benzene derivatives of formula (3):

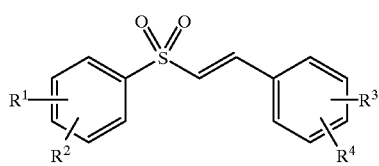

(3)

wherein $R^1$ and $R^2$ are the same or different, and each independently represent a hydrogen, fluorine, or chlorine atom, or a lower alkyl, lower alkoxy, nitro, cyano, amino, lower alkylamino, di(lower alkyl)amino, acyl, or alkoxycarbonyl group, and $R^3$ and $R^4$ are the same or different and each idenpendently represent a hydrogen, fluorine, or chlorine atom, or a lower alkyl, lower alkoxy, nitro, cyano, amino, lower alkylamino, di(lower alkyl)amino, acyl, or alkoxycarbonyl group, and two adjacent $R^3$ and $R^4$ may bond each other at their terminals to form a fused ring together with the benzene ring to which said $R^3$ and $R^4$ are bonded, which comprises the steps of:
(a) reacting a 2-(arylsulfonyl)ethanol of formula (1):

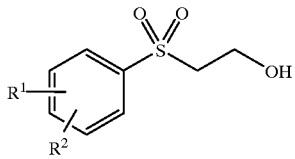

(1)

wherein $R^1$ and $R^2$ are as the same as defined above, with an acid anhydride in the presence of a base, and (b) subjecting the resulting reaction solution in step (a) to a reaction with an aromatic halide of formula (2):

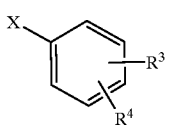

(2)

wherein X represents a chlorine, bromine, or iodine atom, and $R^3$ and $R^4$ are the same as defined above, in the presence of a palladium catalyst and a base.

DESCRIPTION OF THE PREFERRED EMBODIMENTS

First, a description will be made to the step (a) as below.

Examples of the lower alkyl groups for $R^1$ and $R^2$ in 2-(arylsulfonyl)ethanol of the formula (1) include, for example, a straight or branched alkyl group having 1 to 6 carbon atoms, such as methyl, ethyl, propyl, butyl, pentyl, hexyl, isopropyl, isobutyl, sec-butyl, tert-butyl, isopentyl, neopentyl, and tert-pentyl groups.

Examples of the lower alkoxy group for $R^1$ and $R^2$ include, for example, a straight or branched alkoxy group having 1 to 6 carbon atoms, such as methoxy, ethoxy, propoxy, butoxy, pentoxy, hexoxy, isopropoxy, isobutoxy, sec-butoxy, tert-butoxy, isopentoxy, neopentoxy, and tert-pentoxy groups.

Examples of the lower alkylamino group for $R^1$ and $R^2$ include an amino group substituted with one lower alkyl group, wherein the lower alkyl group may be one of those as described above. Examples of such lower alkylamino group are methylamino, ethylamino, and tert-butylamino groups.

Examples of the di(lower alkyl)amino group include an amino group substituted with two lower alkyl groups, wherein the lower alkyl groups may be those as described above. Specific examples of such di(lower alkyl)amino group are dimethylamino, diethylamino, methylethylamino, and tert-butylmethylamino groups.

Examples of the acyl group may include, for example, aliphatic acyl groups having 2 to 8 carbon atoms, such as acetyl, propionyl, butyryl, isobutyryl, valeryl, isovaleryl, and trimethylacetyl groups, and aromatic acyl groups such as benzoyl group.

Examples of the alkoxycarbonyl group may include those groups consisting of a lower alkyl group as described above and a carbonyl group, such as methoxycarbonyl, ethoxycarbonyl, propoxycarbonyl, isopropoxycarbonyl, butoxycarbonyl, and tert-butoxycarbonyl groups.

Specific examples of such 2-(arylsulfonyl)ethanol of formula (1) include:

2-(phenylsulfonyl)ethanol, 2-(4-chlorophenylsulfonyl)ethanol,
2-(3,4-dichlorophenylsulfonyl)ethanol, 2-(4-fluorophenylsulfonyl)ethanol,
2-(4-methylphenylsulfonyl)ethanol, 2-(2,4-dimethylphenylsulfonyl)ethanol,
2-(4-ethylphenylsulfonyl)ethanol, 2-(4-isobutylphenylsulfonyl)ethanol,
2-(4tert-butylphenylsulfonyl)ethanol, 2-(4-methoxyphenylsulfonyl)ethanol,
2-(3, 4-dimethoxyphenylsulfonyl)ethanol,
2-(4-tert-butoxyphenylsulfonyl)ethanol, 2-(3-aminophenylsulfonyl)ethanol,
2-(3-methylaminophenylsulfonyl)ethanol,
2-(3-ethylaminophenylsulfonyl)ethanol,
2-(3-dimethylaminophenylsulfonyl)ethanol,
2-(3-diethylaminophenylsulfonyl)ethanol, 2-(3-nitrophenylsulfonyl)ethanol,
2-(4-cyanophenylsulfonyl)ethanol, 2-(3-acetylphenylsulfonyl)ethanol,
2-(4-benzoylphenylsulfonyl)ethanol,
2-(4-methoxycarbonylphenylsulfonyl)ethanol, and the like.

The 2-(arylsulfonyl)ethanols may readily be prepared, for example, by a process in which a thiophenol and ethylene oxide or 2-chloroethanol are reacted to obtain a sulfide, which is then oxidized (see, for example, Japanese Patent Publication Kokoku No. H4-17182 (1992); Bull. Korean Chem. Soc., 16, 670 (1995)). Alternatively, the substituent(s) on the aromatic ring may be introduced after the sulfone compound has been obtained.

The reaction of 2-(arylsulfonyl)ethanol of the formula (1) with an acid anhydride in the presence of a base, may be conducted by mixing the 2-(arylsulfonyl)ethanol of formula (1), the acid anhydride, and the base. The mixing method is not specifically restricted, and for example, may be such a method in which the acid anhydride and the base are added to the 2-(arylsulfonyl)ethanol of formula (1), or the 2-(arylsulfonyl)ethanol of formula (1) and the base are added to the acid anhydride. Said addition may be continuous or at one time.

The acid anhydrides include, for example, an acid anhydride of formula (4):

$$Q_2O$$

wherein Q represents a hydrocarbylcarbonyl group which may be substituted (e.g., a carboxylic acid anhydride) or a hydrocarbylsulfonyl group which may be susbtituted (e.g., sulfonic anhydride).

Examples of the hydrocarbyl group herein include
an aliphatic group which may be substituted with a halogen atom (e.g., a (C1–C7)alkyl group, etc.), and
an aromatic group which may be substituted with an (C1–C4)alkyl group (e.g. a phenyl, or a tolyl group) or a halogen atom.

Specific examples of the carboxylic anhydrides include, for example, aliphatic carboxylic anhydrides such as acetic anhydride, propionic anhydride, and trifluoroacetic anhydride, and aromatic carboxylic anhydrides such as benzoic anhydride.

The sulfonic anhydrides include, for example, alkanesulfonic anhydrides such as methanesulfonic anhydride and trifluoromethanesulfonic anhydride, and aromatic sulfonic anhydrides such as p-toluenesulfonic anhydride.

The amount of acid anhydride is usually one mole or more per mol of 2-(arylsulfonyl)ethanol, and although the upper limit is not specifically limited, the amount is usually 3 moles or less, and preferably 2 moles or less, from an economic point of view.

The bases may include, for example, tertiary amines, pyridines, alkali metal carbonates, alkali metal bicarbonates, alkali metal carboxylates, alkali metal phosphates, and mixtures thereof. Among others tertiary amines are preferably used.

Examples of the tertiary amine include an amine substituted with three groups selected from a saturated(C1–C8) or unsaturated (C2–C8) aliphatic group which may be substituted with an aryl group (e.g. phenyl or naphthyl) and an aromatic group such as an aryl group as defined above. Specific examples of the tertiary aliphatic or aromatic amines such as trimethylamine, triethylamine, tripropylamine, triisopropylamine, tributylamine, triisobutylamine, diisopropylethylamine, triallylamine, N,N-dimethylbenzylamine, N,N-dimethylaniline and N,N,N',N'-tetramethylethylenediamine. In addition said tertiary amine include a heterocylic tertiary amine selected from 1,5-diazabicyclo[4.3.0]non-5-ene, 1,8-diazabicyclo [5.4.0] undec-7-ene, N-methylpyrrolidine, N-methylpiperidine, N-methylmorpholine,.

Examples of pyridines include a pyridine compound which may be substituted with a (C1–C4) alkyl group. Specific examples of which include pyridine and picoline.

Examples of alkali metal carbonate include lithium carbonate, sodium carbonate, potassium carbonate, cesium carbonate, and examples of alkali metal bicarbonate are sodium bicarbonate and potassium bicarbonate.

Examples of alkali metal carboxylate include sodium acetate and potassium acetate, and an example of alkali metal phosphate includes potassium tertiary phosphate.

The amount of the base is usually 2 moles or more per mol of 2-(arylsulfonyl)ethanol of formula (1) to obtain a vinylsulfone compound of formula (5) below as a product in step (a). 3 moles or more of the base are used per mol of 2-(arylsulfonyl)ethanol in view of the use of a base in the next step described hereinbelow. Although the upper limit is not specifically limited, the amount is usually 10 moles or less, and preferably 5 moles or less, from an economic point of view.

The reaction temperature is usually in the range from –30 to 150° C., and preferably from –10 to 100° C.

The reaction is usually conducted in the presence of solvent, and the solvent may be, for example, an ether solvent such as dimethoxyethane, tetrahydrofuran, or diethyl ether,
an aromatic hydrocarbon solvent such as toluene, xylene, chlorobenzene, or dichlorobenzene,
an aliphatic hydrocarbon solvent such as hexane or heptane,
a halogenated hydrocarbon solvent such as dichloromethane, 1,2-dichloroethane, chloroform, or carbon tetrachloride,
an aprotic polar solvent such as N,N-dimethylformamide, dimethylsulfoxide, or acetonitrile, or a mixture thereof. Although the amount of solvent used is not specifically limited, it is usually 50 parts by weight or less to one part by weight of 2-(arylsulfonyl)ethanol of formula (1) from the volume efficiency and other factors. The solvent may be added in advance to the 2-(arylsulfonyl)ethanol of formula (1), acid anhydride, or base. When a liquid base such as the above described base is used, the base may also serve as the solvent, and in that case, the amount of such base which is also used as a solvent is usually 50 parts by weight or less to 1 part by weight of 2-(arylsulfonyl)ethanol of formula (1), although the upper limit is not specifically limited.

The resulting reaction solution in Step (a) contains a vinyl sulfone compound having a vinyl group in place of a hydroxyethylene group in the 2-(arylsulfonyl)ethanol of formula (1) above.

In the following paragraphs, Step (b) is explained. In this step the resulting reaction solution obtained in the above-described Step (a) is subjected to Step (b), which means that said reaction solution is supplied as it is without isolating a product therefrom.

In an aromatic halide of formula (2), The substituent X and $R^3$ and $R^4$ will be explained.

Examples of the lower alkyl, lower alkoxy, lower alkylamino, di(lower alkyl)amino, acyl, and alkoxycarbonyl groups for $R^3$ and $R^4$ include the same groups as described above for $R^1$ and $R^2$.

Examples of a fused ring formed from two adjacent $R^3$ and $R^4$ which are bonded together at their terminals to form a ring together with the benzene ring to which said $R^3$ and $R^4$ are bonded for the aromatic halide of formula (2) include: indans, benzofurans, indoles, indolines, naphthalenes, tetralins, coumarins, isocoumarins, benzopyrans, quinolines, isoquinolines, and the like, which may be substituted with a group such as N-methylpyrrolidine-2-ylmethyl group and the like.

Examples of the aromatic halides of formula (2) include, for example, aromatic bromides such as bromobenzene, 4-chlorobromobenzene, 3,4-dichlorobromobenzene, 4-fluorobromobenzene, 3-chloro-4-fluorobromobenzene, o-bromotoluene, m-bromotoluene, p-bromotoluene, 4-bromoethylbenzene, 4-bromoisobutylbenzene, 4-bromo-tert-butylbenzene, 5-bromo-m-xylene, 4-bromoanisole, 4-bromophentole, 3,4-dimethoxybromobenzene, 4-tert-butoxybromobenzene, 3-bromonitrobenzene, 3-bromoaniline, N-methyl-3-bromoaniline, N-ethyl-3-bromoaniline, N,N-dimethyl-3-bromoaniline, N,N-diethyl-3-bromoaniline, 4-cyanobromobenzene, 3-acetylbromobenzene, methyl 4-bromobenzoate, 4-bromoindan, 5-bromoindan, 5-bromobenzofuran, 5-bromo-2,3-dihydrobenzofuran, 5-bromoindole, 5-bromoindoline, 5-bromonaphthalene, 6-bromonaphthalene, 5-bromotetralin, 6-bromotetralin, 6-bromocoumarin, 6-bromoisocoumarin, 6-bromo-2H-benzopyran, 6-bromoquinoline, 6-bromo-1,2,3,4-tetrahydroquinoline, and 6-bromo-1,2,3,4-isoquinoline, as well as aromatic iodides in which the "bromo" in the above-listed compounds is replaced with "iodo", and aromatic chlorides in which the "bromo" in the above-listed compounds is replaced with "chloro". The aromatic bromides and aromatic iodides are preferrred because of their reactivity.

The amount of the aromatic halide to be used is usually 0.5 to 5 moles per mol of 2-(arylsulfonyl)ethanol of the formula (1) used in the preceding step.

Examples of palladium catalyst include zero-valent or bivalent palladium catalysts such as palladium chloride, palladium acetate, palladium oxide, palladium hydroxide, tetrakis(triphenylphosphine)palladium, dichlorobis(triphenylphosphine)palladium, bis(triphenylphosphine) palladium acetate, tris(dibenzylideneacetone)dipalladium, bis(acetonitrile)dichloropalladium, and bis(benzonitrile) dichloropalladium, and the amount thereof is usually in the range from 0.001 to 0.2 mole per mol of 2-(arylsulfonyl) ethanol of the formula (1) used in the preceding step.

In addition to such palladium catalyst, an additive such as a tertiary phosphine, quaternary phosphonium salt, N,N-substituted amino acid, or the like are preferred in order to improve the activity of the reaction, and among others, tertiary phosphines are particularly preferred for this purpose.

Examples of tertiary phosphine include triphenylphosphine, tri(o-tolyl)phosphine, tri(o-tolyl) phosphine, tri(p-methoxyphenyl)phosphine, tri(p-fluorophenyl)phosphine, triethylphosphine, tributylphosphine, tri(tert-butyl)phosphine, tricyclohexylphosphine, 1,2-bis(diphenylphosphino)ethane, 1,3-bis(diphenylphosphino)propane, 1,4-bis(diphenylphosphino)butane, and the like.

Examples of quaternary phosphonium salt include tetraphenylphosphonium bromide, tetraphenylphosphonium chloride and the like, and examples of N,N-substituted amino acid include N,N-dimethylglycine.

The amount of the additive is usually 50 moles or less, and preferably 30 moles or less, per mol of palladium catalyst used.

The reaction is usually conducted in the presence of a base. Examples of the base include one of those bases as described above, and a silver compound selected from silver nitrate, silver carbonate, silver acetate and the like, and a thallium compound such as thallium acetate and the like. Among the bases, tertiary amines are especially preferred, and practically, the same base as that used in Step (a) is used.

When the amount of the base to be used in Step (a) is 3 moles or more per mol of the 2-(arylsulfonyl)ethanol of formula (1), it is not necessary to add an additional amount of the base. The amount of the base is 3 moles or more, inclusive of that used in Step (a), per mol of 2-(arylsulfonyl) ethanol of formula (1), and although the upper limit is not specifically limited, the amount is usually 10 moles or less, preferably 5 moles or less per mol of 2-(arylsulfonyl)ethanol of formula (1) from an economic point of view.

Furthermore, such reactions are preferably conducted in the presence of a solvent. Examples of the solvent include a solvent used in the above-described Step (a). When a solvent is used in Step (a), there is no need to newly add a solvent. Although the amount of solvent used is not specifically limited, it is usually 50 parts by weight or less per 1 part by weight of the 2-(arylsulfonyl)ethanol of formula (1) used in Step (a) from the volume efficiency and other factors.

This reaction is usually conducted by adding a palladium catalyst, an aromatic halide of formula (2), and if necessary, a base, a solvent, and an additive to the reaction solution obtained in Step (a), wherein the order of addition is not specifically limited.

The reaction temperature is usually in the range from 0 to 150° C., and preferably from 15 to 100° C.

Thus, a 2-(arylsulfonyl)ethanol of the formula (1) and an acid anhydride are reacted in the presence of a base (Step (a)), and the reaction solution obtained is sujected to a reaction with an aromatic halide of the formula (2) in the presence of a palladium catalyst and a base (Step (b)) to obtain a reaction mass containing a desired [2-(arylsulfonyl) ethenyl]benzene derivative of the formula (3).

Said [2-(arylsulfonyl)ethenyl]benzene derivatives of formula (3) can be isolated by, for example, concentrating the obtained reaction mass after, if necessary, filtering it to remove insoluble matter.

The isolated [2-(arylsulfonyl)ethenyl]benzene derivatives may be further purified, for example, by column chromatography, recrystallization, and the like, if necessary.

Examples of [2-(arylsulfonyl)ethenyl]benzene derivative of formula (3) thus obtained include [2-(phenylsulfonyl) ethenyl]benzene, [2-(phenylsulfonyl)ethenyl]-4- chlorobenzene, [2-(phenylsulfonyl)ethenyl]-3-chloro-4-fluorobenzene, [2-(phenylsulfonyl)ethenyl]-2-methylbenzene, [2-(phenylsulfonyl)ethenyl]-4-ethylbenzene, [2-(phenylsulfonyl)ethenyl]-4-methoxybenzene, [2-(phenylsulfonyl)ethenyl]-3,4-dimethoxybenzene, [2-(phenylsulfonyl)ethenyl]-3-nitrobenzene, [2-(phenylsulfonyl)ethenyl]-3-aminobenzene, [2-(phenylsulfonyl)ethenyl]-3-(dimethylamino)benzene, [2-(phenylsulfonyl)ethenyl]-3-acetylbenzene, [2-(phenylsulfonyl)ethenyl]-4-cyanobenzene, [2-(phenylsulfonyl)ethenyl]-4-methoxycarbonylbenzene, 5-[2-(phenylsulfonyl)ethenyl]indan, 5-[2-(phenylsulfonyl)ethenyl]benzofuran, 5-[2-(phenylsulfonyl)ethenyl]indole, 5-[2-(phenylsulfonyl)ethenyl]indoline, 5-[2-(phenylsulfonyl)ethenyl]naphthalene, 6-[2-(phenylsulfonyl)ethenyl]tetralin, 6-[2-(phenylsulfonyl)ethenyl]coumarin, 6-[2-(phenylsulfonyl)ethenyl]-2H-benzopyran, 6-[2-(phenylsulfonyl)ethenyl]quinoline, 5-[2-(phenylsulfonyl)ethenyl]-3-(N-methylpyrrolidine-2-ylmethyl)-1H-indole, [2-(4-chlorophenylsulfonyl)ethenyl]benzene, [2-(4-fluorophenylsulfonyl)ethenyl]benzene, [2-(4-methylphenylsulfonyl)ethenyl]benzene, [2-(4-methoxyphenylsulfonyl)ethenyl]benzene, [2-(3-dimethylaminophenylsulfonyl)ethenyl]benzene, [2-(3-nitrophenylsulfonyl)ethenyl]benzene, [2-(4-cyanophenylsulfonyl)ethenyl]benzene, [2-(3-acetylphenylsulfonyl)ethenyl]benzene, and [2-(4-methoxycarbonylphenylsulfonyl)ethenyl]benzene.

According to the present invention, desired [2-(arylsulfonyl)ethenyl]benzene derivatives can be obtained more safely without using solid aryl vinyl sulfones which must be handled with care.

EXAMPLES

The present invention is illustrated below in more detail by the following examples, but are not to be construed to limit the present invention thereto.

Example 1

To 0.186 g (1.0 mmol) of 2-(phenylsulfonyl)ethanol, 3 ml of acetonitrile was added, followed by 0.19 g (1.1 mmol) of methanesulfonic anhydride and 0.56 ml (4.0 mmol) of triethylamine, and the mixture was stirred for 5 hours at the internal temperature of 50° C. Subsequently, 0.19 ml (1.5 mmol) of o-iodotoluene, 0.11 g (0.05 mmol) of palladium acetate, and 0.067 g (0.22 mmol) of tri(o-tolyl)phosphine were added thereto, and the mixture was then refluxed for 16 hours. After cooled to room temperature, the reaction mixture was concentrated and purified by column chromatography (hexane/ethyl acetate=80/20) to obtain 0.21 g of [2-(phenylsulfonyl)ethenyl]-2-methylbenzene. Yield: 80%.

Example 2

[2-(Phenylsulfonyl)ethenyl]-2-methylbenzene was obtained in a yield of 50% in the same manner as in Example 1 except that 1.1 mmol of trifluoromethanesulfonic anhydride was used in place of 0.19 g (1.1 mmol) of methanesulfonic anhydride, Example 3

[2-(Phenylsulfonyl)ethenyl]-2-methylbenzene was obtained in a yield of 50% in the same manner as in Example 1 except that 1.1 mmol of trifluoroacetic anhydride was used in place of 0.19 g (1.1 mmol) of methanesulfonic anhydride.

Example 4

[2-(Phenylsulfonyl)ethenyl]-2-methylbenzene was obtained in a yield of 80% in the same manner as in Example 1 except that 1.1 mmol of p-toluenesulfonic anhydride was used in place of 0.19 g (1.1 mmol) of methanesulfonic anhydride.

Example 5

In the same manner as in Example 1 except that 0.18 ml (1.5 mmol) of o-bromotoluene was used in place of 0.19 ml (1.5 mmol) of o-iodotoluene, 0.059 g of [2-(phenylsulfonyl)ethenyl]-2-methylbenzene was obtained. Yield: 23%.

Example 6

To 0.186 g (1.0 mmol) of 2-(phenylsulfonyl)ethanol, 3 ml of acetonitrile was added, followed by 0.19 g(1.1 mmol) of methanesulfonic anhydride and 0.56 ml (4.0 mmol) of triethylamine, and the mixture was stirred for 5 hours at an internal temperature of 50° C. Subsequently, 0.29 g (1.5 mmol) of 5-bromoindole, 0.011 g (0.05 mmol) of palladium acetate, and 0.067 g (0.22 mmol) of tri(o-tolyl)phosphine were added, and the mixture was then refluxed for 17 hours. After cooled to room temperature, the reaction mixture was concentrated and purified by column chromatography (hexane/ethyl acetate=70/30) to obtain 0.066 g of 5-[2-(phenylsulfonyl)ethenyl]indole. Yield: 23%.

Example 7

In the same manner as in Example 6 except that 1.1 mmol of p-toluenesulfonic anhydride was used in place of 0.19 g (1.1 mmol) of methanesulfonic anhydride, 0.0286 g of 5-[2-(phenylsulfonyl)ethenyl]indole was obtained. Yield: 10%.

Example 8

In the same manner as in Example 6 except that 1.1 mmol of trifluoroacetic anhydride was used in place of 0.19 g (1.1 mmol) of methanesulfonic anhydride, 0.12 g of 5-[2-(phenylsulfonyl)ethenyl]indole was obtained. Yield: 42%.

Example 9

In the same manner as in Example 6 except that 1.1 mmol of benzoic anhydride was used in place of 0.19 g (1.1 mmol) of methanesulfonic anhydride, 0.046 g of 5-[2-(phenylsulfonyl)ethenyl]indole was obtained. Yield: 16%.

Example 10

In the same manner as in Example 6 except that 1.1 mmol of trifluoromethanesulfonic anhydride was used in place of 0.19 g (1.1 mmol) of methanesulfonic anhydride, 0.060 g of 5-[2-(phenylsulfonyl)ethenyl]indole was obtained. Yield: 21%.

Example 11

To 0.186 g (1.0 mmol) of 2-(phenylsulfonyl)ethanol, 3 ml of acetonitrile was added, followed by 0.19 g (1.1 mmol) of methanesulfonic anhydride and 0.56 ml (4.0 mmol) of triethylamine, and the mixture was stirred for 5 hours at the internal temperature of 50° C. Subsequently, 0.37 g (1.5 mmol) of p-iodophenetole, 0.011g (0.05 mmol) of palladium acetate, and 0.067 g (0.22 mmol) of tri(o-tolyl)phosphine were added thereto, and the mixture was then refluxed for 17 hours. After cooled to room temperature, the reaction mixture was concentrated and purified by column chromatography (hexane/ethyl acetate=80/20) to obtain 0.158 g of [2-(phenylsulfonyl)ethenyl]-4-ethoxybenzene. Yield: 55%.

Example 12

To 0.186 g (1.0 mmol) of 2-(phenylsulfonyl)ethanol, 3 ml of acetonitrile was added, followed by 0.19 g (1.1 mmol) of methanesulfonic anhydride and 0.56 ml (4.0 mmol) of triethylamine, and the mixture was stirred for 5 hours at an internal temperature of 50° C. Subsequently, 0.22 ml (1.5 mmol) of 1-iodonaphthalene, 0.11 g (0.05 mmol) of palladium acetate, and 0.067 g (0.22 mmol) of tri(o-tolyl) phosphine were added thereto, and the mixture was then refluxed for 17 hours. After cooled to room temperature, the reaction mixture was concentrated and purified by column chromatography (hexane/ethyl acetate=80/20) to obtain 0.194 g of [2-(phenylsulfonyl)ethenyl]naphthalene. Yield: 66%.

Example 13

In the same manner as in Example 6 with the exceptions that 1.1 mmol of trifluoroacetic anhydride was used in place of 0.19 g (1.1 mmol) of methanesulfonic anhydride and that 1.5 mmol of 5-iodoindole was used in place of 0.29 g (1.5 mmol) of 5-bromoindole, 0.146 g of 5-[2-(phenylsulfonyl)ethenyl]indole was obtained. Yield: 52%.

Example 14

0.204 g (1.1 mmol) of 2-(phenylsulfonyl)ethanol dissolved in 1.0 ml of dimethylformamide was added to a two-necked flask which had been dried under nitrogen atomosphere with flame. 0.17 ml (1.1 mmol) of trifluoroacetic anhydride and 0.62 ml (4.4 mmol) of triethylamine were added thereto and the resulting solution was stirred for 5 hrs at 50° C.

In a separate reaction flask 0.011 g (5 mol %) of palladium acetate and 0.067 g (22 mol %) of tri-o-tolylphosphine in 0.5 ml of dimethylformamide were stirred for 10 min. The resulting suspension solution was added to the two-necked reaction flask together with 0.5 ml of dimethylformamide as rinse solution, followed by the addition of 0.293 g (1.0 mmol) of 5-bromo-3-(N-methylpyrolidine-2-ylmethyl)-1H-indole dissolved in 1.0 ml of dimethylformamide, and resulting reaction mixture was refluxed for 17 hrs while preventing exposure to light.

To the reaction mixture was added water, and extracted with ethyl acetate. Obtained water layer was washed thrice with ethyl acetate. Obtained organic layers were combined and washed with saline, and dried over anhydrous sodium sulfate, and concentrated to give a residue.

The obtained residue was then subjected to silica gel column chromatography. After impurities were eluted with methanol/chloroform/concentrated aqueous ammonia (50:50:1), desired product was eluted with dichloromethane/methanol/concentrated aqueous ammonia solution (90:10:1). Eluated solution was concentrated to give 0.167 g of 5-(2-phenylsulfonylethenyl)-3-N-methyl-pyrrolidin-2-ylmethyl)-1H-indole. Yield: 57%.

What is claimed is:

1. A process for producing a [2-(arylsulfonyl)ethenyl] benzene derivative of formula (3):

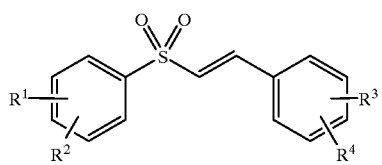

(3)

wherein $R^1$ and $R^2$ are the same or different and each independently represent a hydrogen, fluorine, or chlorine atom, or a lower alkyl, lower alkoxy, nitro, cyano, amino, lower alkylamino, di(lower alkyl)amino, acyl, or alkoxycarbonyl group, and $R^3$ and $R^4$ are the same or different and each independently represent a hydrogen, fluorine, or chlorine atom, or a lower alkyl, lower alkoxy, nitro, cyano, amino, lower alkylamino, di(lower alkyl)amino, acyl, or alkoxycarbonyl group, and two adjacent $R^3$ and $R^4$ may bond each other at their terminals to form a fused ring together with the benzene ring to which said $R^3$ and $R^4$ are bonded, which comprises the steps of:
(a) reacting a 2-(arylsulfonyl)ethanol of formula (1):

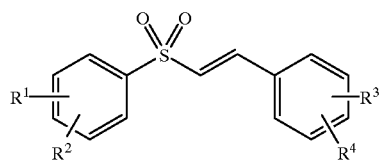

(3)

wherein $R^1$ and $R^2$ are as defined above, with an acid anhydride in the presence of a base, and (b) subjecting the resulting reaction solution in step (a) to a reaction with an aromatic halide of formula (2):

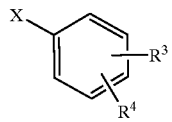

(2)

wherein X represents a chlorine, bromine, or iodine atom, and $R^3$ and $R^4$ are the same as defined above, in the presence of a palladium catalyst and a base.

2. A process according to claim 1, wherein the acid anhydride is a carboxylic anhydride or a sulfonic anhydride.

3. A process according to claim 2, wherein the carboxylic anhydride is acetic anhydride, trifluoroacetic anhydride, or benzoic anhydride.

4. A process according to claim 2, wherein the sulfonic anhydride is methanesulfonic anhydride, trifluoromethanesulfonic anhydride, or p-toluenesulfonic anhydride.

5. A process according to claim 1, wherein said reaction in Step (b) is in the presence of a tertiary phosphine.

6. A process according to claim 1, wherein the bases used in Steps (a) and (b) are the same or different tertiary amine.

7. A process according to claim 1, wherein
the lower alkoxy group for $R^1$ to $R^4$ is a (C1–C6)alkyl group,
the lower alkoxy group for $R^1$ to $R^4$ is a (C1–C6)alkoxy group,
the lower alkylamino for $R^1$ to $R^4$ is a (C1–C6)alkylamino group,
the di(lower alkyl)amino group for $R^1$ to $R^4$ is a di((C1–C6)alkyl)amino group,
the acyl group for $R^1$ to $R^4$ is a (C2–C8)acyl group,
the alkoxycarbonyl group for $R^1$ to $R^4$ is a (C1–C6) alkylcarbonyl group, and
a fused ring formed from two adjacent $R^3$ and $R^4$ which are bonded together at their terminals to form a ring together with the benzene ring to which the $R^3$ and $R^4$ are bonded is selected from indan, benzofuran, indole, indoline, naphthalene, tetralin, coumarin, isocoumarin, benzopyran, quinoline, and isoquinoline, all of which may be substituted with an N-methylpyrrolidine-2-ylmethyl group; and the palladium catalyst is selected from palladium chloride, palladium acetate, palladium oxide, palladium hydroxide, tetrakis(triphenylphosphine) palladium, dichlorobis(triphenylphosphine)palladium, bis(triphenylphosphine)palladium acetate, tris (dibenzylideneacetone)dipalladium, bis(acetonitrile) dichloropalladium, and bis(benzonitrile) dichloropalladium.

* * * * *